United States Patent [19]

Potter

[11] Patent Number: 5,074,632
[45] Date of Patent: Dec. 24, 1991

[54] FIBER OPTIC DIFFUSERS AND METHODS FOR MANUFACTURE OF THE SAME

[75] Inventor: William R. Potter, Grand Island, N.Y.

[73] Assignee: Health Research, Inc., Buffalo, N.Y.

[21] Appl. No.: 490,048

[22] Filed: Mar. 7, 1990

[51] Int. Cl.⁵ .............................................. G02B 6/26
[52] U.S. Cl. ..................................................... 385/31
[58] Field of Search .............. 350/96.15, 96.29, 96.16, 350/96.20, 320

[56] References Cited

U.S. PATENT DOCUMENTS 4,660,925 4/1987 McCaughan, Jr. .......... 350/96.20 X
4,693,556 9/1987 McCaughan, Jr. .......... 350/96.20 X Primary Examiner—William L. Sikes
Assistant Examiner—Phan T. Heartney
Attorney, Agent, or Firm—Irell & Manella

[57] ABSTRACT

The present invention relates to improvements on fiberoptic diffusers for use in PDT and methods of making the same. This invention discloses a fiberoptic cylindrical diffuser dispersing light outwardly in a cylindrical scattering pattern which includes a fiber with a jacket-stripped core tip, a thin layer of scattering medium coated on the bare core tip, and a sleeve member with a closed end enclosing the fiber tip without touching the scattering medium and fixed on the jacket of the fiber. The sleeve member may include a tapered head. The present invention also discloses a fiberoptic spherical diffuser radiating light outwardly in a spherical scattering pattern. The spherical diffuser comprises a fiber with a jacket-stripped core tip, a bushing member with open ends circumferentially surrounding the core tip and fixed on the jacket of the fiber, and a scattering medium enclosing a portion of the bushing member and the fiber core tip in a spherical form.

27 Claims, 2 Drawing Sheets

FIBER OPTIC DIFFUSERS AND METHODS FOR MANUFACTURE OF THE SAME

BACKGROUND OF THE INVENTION

This invention relates to a fiber optic apparatus for producing an approximately uniform scattered light output, and particularly to improvements on two types of fiberoptic diffusers which can be used in a biological environment, and methods of manufacturing the same.

The method known as "photodynamic therapy" (PDT) has been widely used in recent years in treatment for cancers or tumors, and other diseases in humans and even in animals. Reference is made to U.S. Pat. No. 4,889,129 for a discussion of particulars of one such PDT method and apparatus for practicing the method. There are three types of optical devices which are mainly used in PDT for light distribution at the treating region. The fiber optic microlens is one type of device which can transfer a divergent light beam to an area of accessible tissue surfaces. The fiber optic cylindrical diffuser or "line source" is another type which has a cylindrical scattering pattern of light output with respect to the central axis of the optical fiber, and can be used in a cylindrical geometry for application to areas such as a bronchus or esophagus. The fiber optic spherical diffuser or "light bulb" is the third type of device which produces a spherical scattering light field. The spherical diffuser is usually applied in treatment to approximately spherical cavities, e.g. the bladder or a surgically created cavity resulting from the resection of the bulk of a tumor.

A typical example of a fiber optic cylindrical diffuser and a method of making the same is disclosed in U.S. Pat. No. 4,660,925 issued on Apr. 28, 1987 to James S. McCaughen, Jr. The cylindrical diffuser disclosed by the MaCaughan patent includes an optical fiber with an exposed core portion at one end, a scattering medium coated on the exposed core portion and on the sheathing of the fiber adjacent thereto, and an end-open tube adhered on the scattering medium. The process of manufacturing the diffuser mainly includes the steps of stripping the cladding and sheathing of the fiber at one end of the fiber to provide a length of exposed fiber core, polishing the exposed core, coating the exposed core and the adjacent sheathing with a scattering medium, tightly inserting the scattering medium into the tube, filling interstices between the earlier coated scattering medium and the tube with the scattering medium, and excluding the entrapped air.

A typical fiber optic spherical diffuser and a method of making the same are shown by the U.S. Pat. No. 4,693,556 issued on Sept. 15, 1987 to James S. McCaughan, Jr. The method mainly includes the steps of removing the cladding and sheathing of an optical fiber at one end to provide an exposed core portion, polishing the exposed core portion, and coating the exposed core portion and the adjacent sheathing of the fiber layer by layer with a scattering medium until a scattering sphere is formed.

In photodynamic therapy, the basic requirements for the fiber optic diffusers are that the light distribution must be as uniform as possible within a volume of tissue containing a tumor, and the mechanical properties must be reliable. If the fiber optical diffuser assembly breaks on insertion or during treatment, the light distribution will be inadequate at best. Furthermore, there is a possibility that a piece of the broken fiber will be left behind and if elevated oxygen concentration is present the danger of fire exists because of the higher power density present at the broken end of the fiber. In addition, rigidity of the fiber optic diffuser is also an important requirement in PDT. This is because the path of the fiber assembly in a channel of a flexible endoscope and in a tumor should be controlled by the direction of insertion rather than the irregular mechanical properties of the tissue or tumor. It is also desirable that the fiber optic diffusers have a low power loss and maximum power handling ability.

These requirements are not well satisfied by the conventional devices due to the shortcomings in their structures or the methods of making them.

The present invention is an improvement on the prior fiberoptic diffusers including the prior fiberoptic cylindrical diffusers and fiberoptic spherical diffusers, and on the methods of manufacturing the same.

OBJECT OF THE INVENTION

It is an object of the present invention to provide a fiber optic diffuser which has an approximately uniform scattering light output and good mechanical properties.

It is another object of the present invention to provide a fiber optic diffuser for use in a biological environment which has good optical properties and good mechanical properties.

It is still another object of the present invention to provide methods of manufacturing the fiber optic diffusers of the present invention which simplify the conventional process.

It is still another object of the present invention to provide a fiber optic cylindrical diffuser having an approximately uniform light output in a cylindrical scattering pattern with respect to the central axis of the fiber, and good mechanical properties, and a method of making the same.

It is still another object of the present invention to provide a fiber optic cylindrical diffuser with a low enough power loss, which can handle up to at least 600 mw/cm of 630 nm light continuously without damage, and has a good mechanical strength and rigidity to allow a smooth insertion of the fiber assembly through the biopy channel of a flexible endoscope and into a tumor along a straight pass.

It is a further object of the present invention to provide a fiber optic spherical diffuser with an approximately uniform light output in a spherical scattering pattern, and good mechanical properties, and a method of making the same.

It is still a further object of the present invention to provide a fiber optic spherical diffuser with sufficiently low power loss, which can handle continuous power levels of at least three watts of 630 nm light without being damaged, and has good physical properties to withstand cold sterilization and to allow a smooth pass through a cytoscope.

It is still a further object of the present invention to provide a scatter composition which can be used in the fiber optic diffusers with improved optical properties.

These and still further objects of the present invention will become apparent hereinafter.

BRIEF SUMMARY OF THE INVENTION

This invention relates to improvements on the fiber optic diffusers for use in PDT. The present invention discloses a fiber optic cylindrical diffuser which includes an optical fiber with a jacket-stripped bare core tip at one end, a thin layer of scattering medium coated on the bare core tip, and a colorless sleeve member enclosing the fiber tip without touching the scattering medium and fixed on the jacket of the fiber. In a preferred embodiment, the sleeve member has a core head at a desired angle with respect to the central axis of the fiber. The sleeve member is preferably threaded on the jacket of the fiber in a water tight seal. In an alternative for a short tip diffuser, the short bare core tip is simply polished to a flat square end face without coating the scattering medium.

The present invention also discloses a fiber optic spherical diffuser which comprises an optical fiber with a jacket-stripped bare core tip, a bushing member circumferentially surrounding the bare core tip and fixed on the jacket of the fiber, and a scattering medium covering the bare core tip and the part of the bushing member in a spherical form. In manufacture, coating of the scattering medium is achieved at one time by using a silicon rubber mold instead of coating layer by layer. The present invention further discloses a scattering mixture which can reduce power loss and enhance the power handling ability of the fiber optic diffusers.

DETAILED DESCRIPTION OF THE INVENTION

Figure 1:
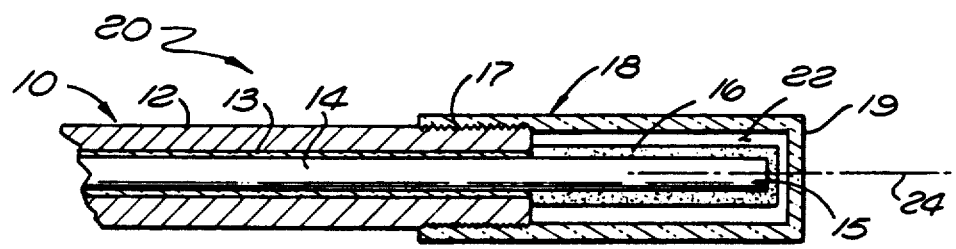
FIG. 1 is a cross-sectional view of a fiber optic cylindrical diffuser of the present invention.

Referring now to the drawings with greater particularity, there is shown in FIG. 1 a fiber optic cylindrical diffuser 20. The cylindrical diffuser 20 includes a longitudinally located optical fiber 10 with a bare fiber core tip 15 coated with a layer of scattering medium 16, and a sleeve 18 enclosing the coated core tip without touching the scattering medium 16 and fixed on the jacket of the fiber 10 adjacent to the core tip 15. The cylindrical diffuser 20 has an approximately uniform light output in an outwardly dispersing cylindrical pattern with respect to the central axis 24 of the fiber 10.

The optical fiber 10 is a quartz optical fiber comprising a quartz core 14 with a diameter of 400 micron. The core 14 is covered by a jacket which consists of a cladding 13 and a sheathing 12. The core 14 is first clad with a transparent polymer layer 13 of 10-20 microns thick. The polymer is then protected from damage by another tefzel sheathing 12 with an outer diameter of about 860 microns. The outer diameter of the sheathing 12 may be changeable. However, the 860 micron diameter is useful because it is ideal to take a rolled thread in the standard size 000-120 (a watchmaker's size). This will be discussed in more detail hereafter. The length of the fiber 10 may be of about two meters long.

One of the ends of the optical fiber 10 is terminated in an SMA style connector (not shown) and connected (SMA to SMA) to a 10 meter length of 100 micron core intermediate jumper fiber which is optically coupled to the output of a laser, such as a 5 mv HeNe laser.

At the opposite end of the optical fiber 10, the sheathing is removed by the use of a wire stripper tool and the cladding removed with the flame of a miniature gas torch or by other proper methods so as to provide a bare core tip portion 15. The length of the bare core tip 15 is preferably 0.5 to 2.5 cm. However, longer lengths are also possible in particular applications.

The bare core tip portion 15 is then covered by a layer of scattering medium 16 which is composed of an optical adhesive; such as the Norland 61 or Epo-Tek 301 epoxy, and a powdered scatterer such as powdered synthetic sapphire (aluminum oxide), diamond dust or zirconium oxide dust. These scatters have refractive indexes to 630 nm light in the 1.7 to 2.2 range. Some other materials may also be suitable. However, the optical adhesive material should match the refractive index of the quartz (about 1.3) as closely as possible to avoid total internal reflection at the quartz-adhesive interface. The scatterer must be of different refractive index from the adhesive. To produce low loss diffusers it is important that the material used have minimal absorbance to the light in the wavelength range of the interested light source, and the adhesive and the powdered scattering material must be optically clear.

The bare core tip 15 is preferably coated with a thin layer of scattering medium 16. This can be accomplished by the following method. First, a thin film of optically clear adhesive is applied to the bare core tip 15. Then, a small artists brush is used to apply a scatterer to the surface of the adhesive-coated fiber core tip. The application of the scatterer is guided by the light transmitted in the fiber from a HeNe laser. During application, the fiber is held parallel to a sheet of white paper (about 1 mm away from the surface). If the paper is between the fiber and the eye of the worker, a good idea of the uniformity of the light field can be obtained from the size and shape of the red illumination. When the desired result has been achieved, the adhesive is cured by UV light for the Norland #61 or by allowing it to cure in the case of the epoxy.

The mechanical requirements are satisfied by the use of a colorless, transparent sleeve 18 which is cylindrical in form and has a closed head portion 19. The sleeve 18 has a bore size larger than the diameter of the scatterer-coated core tip so as to provide an untouching match with the fiber tip and be suitable for being fixed on the jacket of the fiber 10 adjacent to the core tip portion 15. The sleeve 18 can be made of Lexan polycarbonate. In a preferred embodiment of the sleeve 18 as shown in FIG. 1, the sleeve 18 is in threaded connection with the jacket of the fiber 10. The Lexan cylinder (e.g. 1.8 mm outer diameter) is bored out to the diameter necessary for an 000-120 tap (#70 drill). The drill is carried to within 1 to 2 mm of the head portion 19. The cylinder is then tapped (000-120) to a depth of 3 millimeters. The bored length of the Lexan cylinder is at least 3 mm longer than the length of the bare core tip 15. The finished sleeve 18 is then threaded onto the jacket of the fiber 10. The jacket may have had a thread rolled onto it previously by the use of a metal die, or the sleeve 18 may be used to roll the thread at the time of installation. A small amount of epoxy applied to the threads of the sleeve 18 before installation will ensure a water tight seal and strengthen the connection. When properly installed, the sleeve 18 does not touch the scattering medium 16 as shown by a space 22, and thus the optical properties of the diffuser are unaffected by the sleeve 18 which protects the diffuser from mechanical stress during use. This design also makes is easy to manufacture and avoids the nonuniform light output caused by the uneven layer of scattering medium on the core tip which is possible in prior art devices.

Figure 2A:
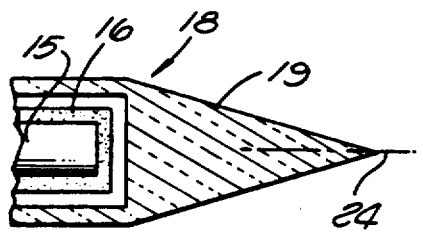
FIG. 2A, 2B and 2C show cross-sectional views of three embodiments of the preferred tapered head of the sleeve member used in a fiber optic cylindrical diffuser of the present invention.
Figure 2B:
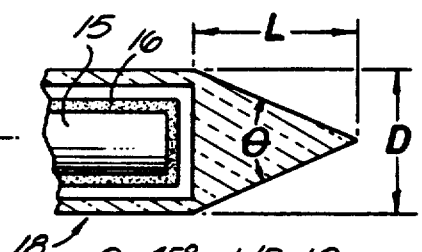
Figure 2C:
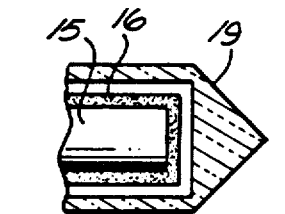

FIG. 2 shows a preferred embodiment of the sleeve 18. The sleeve 18 has a sharpened head portion 19. The angle R of the tapered head 19 is between 30 and 90 degrees and is chosen to facilitate insertion of the fiber diffuser assembly through the endoscope and into a tumor.

This fiberoptic cylindrical diffuser has never failed in experimental use during over one hundred use cycles and has withstood repeated cold sterilization in gluteraldahyde solution ("Cydex") as well as gas sterilization.

Figure 3:
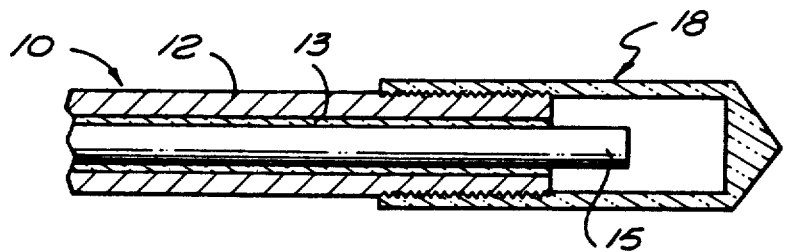
FIG. 3 is a cross-sectional view of an alternate embodiment of a fiber optic cylindrical diffuser in accordance with the present invention.

As for a short fiberoptic diffuser (approximately 1 cm or less), an alternative of the present invention shown in FIG. 3 is to simply cleave fiber 10 and polish the bare core tip 15 to a flat square end face and then thread the sleeve 18 onto the fiber sheathing 12. The diffusing surface of the drilled out sleeve 18 scatters the light spreading out from the polished core end of the fiber 10. In this technique, the fiber is stripped and cleaved carefully so that only the very tip clears the jacket by a short distance, such as less than one mm.

Figure 4:
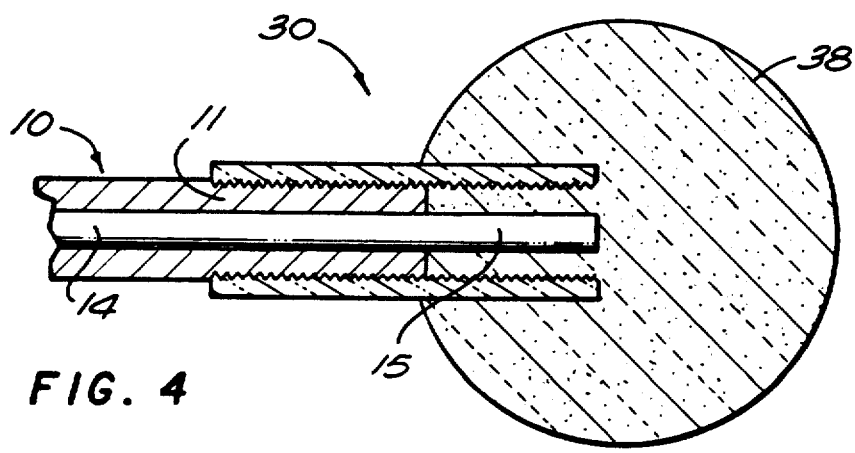
FIG. 4 is a cross-sectional view of a preferred embodiment of a fiber optic spherical diffuser of the present invention.

Turning now to FIG. 4, FIG. 4 shows a fiberoptic spherical diffuser 30 of the present invention. The spherical diffuser 30 includes an optical fiber 10 with a bare core tip 15, a colorless bush member 35 with open ends circumferentially surrounding the core tip 15 and fixed on the jacket 11 of the fiber 10, and a spherical scattering medium 38 enclosing a portion of the bush member 35 and the core tip 15.

The optical fiber 10 still comprises a fiber core 14 protected by a jacket 11 which is composed of a cladding and a sheathing (not shown). The optical fiber 10 has a jacket-stripped tip portion 15, that is, a bare core tip.

Figure 5:
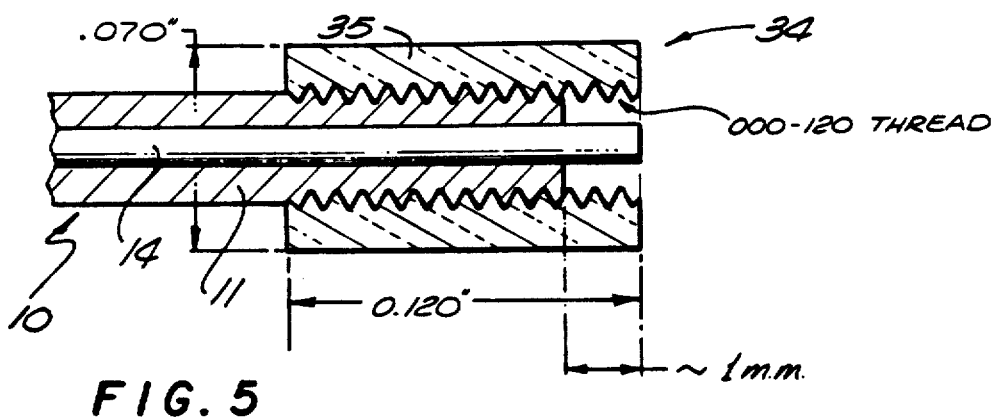
FIG. 5 is a cross-sectional view of a fiber-bushing assembly and a preferred connection between the bushing member and the fiber jacket.

The bush member 35 must have an absorbance as low as possible to the light in the wavelength range of interest. The bushing 35 can be made of Lexan polycarbonate. In a preferred embodiment, the bushing 35 is in a threaded connection with the jacket 11 of the fiber 10. The bushing 35 is tapped by using the 000–120 rolled thread technique as in the case of the cylindrical diffuser of the present invention. A difference is that the bushing member 35 has no closed end. In manufacture, the fiber end is cleaned and polished flat and square, and then threaded into a clear polycarbonate bushing 35 as shown by FIG. 5. FIG. 5 also shows an arrangement of the various sizes of the fiber-bushing assembly 34.

The scattering sphere 38 is composed of a clear optical adhesive and suspended scattering particle of the powdered scattering material. As in the case of the cylindrical diffuser of the present invention, the best materials are those with the least absorbence at the wavelength of interest. Epoxy may be used as the optical adhesive. The index of refraction of the epoxy should match that of the quartz to minimize the reflective loss at the quartz epoxy interface. The epoxy can be any clear colorless product such as epo-tek 301. The sapphire powder, or other low loss scatterers such as diamond dust or powdered zirconia are suitable as the scattering material.

The exact proportions of scatter to epoxy depend upon several factors such as the overall diameter of the diffuser and the refractive index of the particles as well as their size. However, using the minimum amount of scattering material which provides the desired uniformity will result in the lowest loss and maximum power handling ability. The composition by weight preferably ranges between 5% and 20% scatterer, with 7% being about right for sapphire powder.

Figure 6:
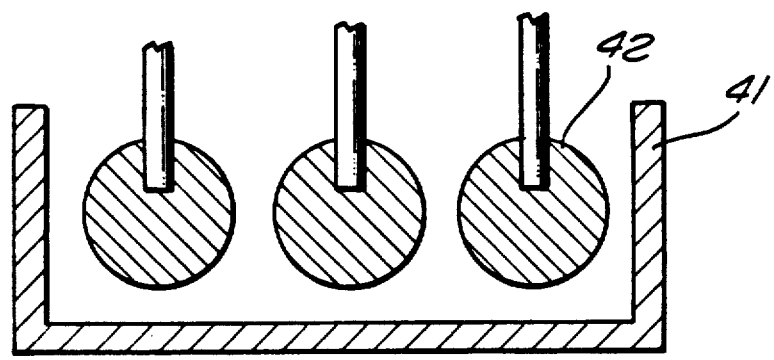
FIG. 6 is a cross-sectional view of an example of a metal mold for making the silicon rubber mold with multi-cavities.

According to the present invention, the production of the sphere can be accomplished cheaply and efficiently by a molding technique employing a reusable silicon rubber mold to form the epoxy scattering sphere. The mold may include multiple cavities so that more than one spherical diffuser can be produced at the same time. As shown by FIG. 6, the silicon rubber mold containing many identical cavities can be produced from a chamber 41 for containing the melted silicon rubber 44 and a metal fixture (not shown) holding an array of identical metal molds of the finished bulb 42. One eighth inch bronze ball bearings bored out and press-filled to one sixteenth inch diameter stainless pin is one way to easily produce such a mold of the bulbs 42. After the silicon rubber has cured the metal plugs can be snapped out of the elastic molds without damage to the mold.

Figure 7:
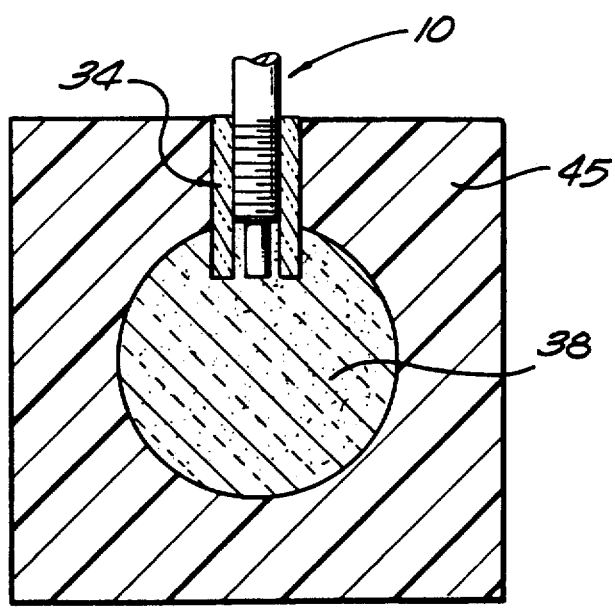
FIG. 7 shows schematically a preferred process of making the scattering sphere of the fiber optic spherical diffuser of the present invention.

Referring now to FIG. 7, the silicon rubber mold 45 is filled from the bottom up slowly by a pipet with the prepared epoxy-scatterer mixture 38 until it is filled completely, and the trapped air and bubbles are removed by tapping and squeezing the mold 45. Then, the finished fiber-bushing assembly 34 is held into the mold by an appropriate fixture and allowed to cure for a certain period at a predetermined temperature, such as two hours at 60° C. During curing of the mixture 38, the position of the end of the fiber 10 within the sphere can be precisely controlled. This is important because the symmetry of the light output depends upon the tip position. The light distribution may be fine tuned by adjusting the position of the fiber tip in the bushing.

In addition, the optical distribution of the diffuser is also related to the process of the pre-pour preparation of the scattering mixture 38. In one embodiment, the epoxy is first mixed with the sapphire for three minutes, then the mixture stands for one hour, mixed again for one minute and then the mixture is degased for 2 minutes with a vacuum pump. The pre-pour curing time may be adjusted in order to get a better light distribution.

The symmetry and light distribution of a finished fiberoptic spherical diffuser can be measured by a turnable measuring device which includes a 5 mv HeNe laser source and a lock-in receiver with a digital volt meter.

While the preferred examples of the present invention have been shown and described, it should be apparent to those skilled in the art that many more modifications are possible without departing from the invention concept herein disclosed. It is intended to cover in the appended claims all such modifications as fall within the true spirit and scope of the invention.

What is claimed is:

1. A cylindrical fiberoptic diffuser, comprising:

an optical fiber with a fiber core and a jacket, said optical fiber including a jacket-stripped core tip portion for emitting light energy, a sleeve means for enclosing said fiber core tip portion without touching the same, said sleeve means having a closed end head portion and an opened end portion fixed on the fiber jacket adjacent to said fiber core tip portion.

2. A fiberoptic diffuser in accordance with claim 1, wherein said fiber core tip portion is coated with a scattering medium.

3. A fiberoptic diffuser in accordance with claims 1 or 2 having a substantially uniform light output in an outwardly cylindrical dispersing pattern with respect to the central axis of said fiber.

4. A fiberoptic diffuser in accordance with claim 3, wherein said sleeve means includes a bore size larger than the diameter of the fiber core or the diameter of said scatterer-coated core tip, and is in a cylindrical form with one end closed.

5. A fiberoptic diffuser in accordance with claim 4, wherein said sleeve means is in threaded connection with the jacket of said fiber.

6. A fiberoptic diffuser in accordance with claim 5, wherein adhesive material is added on the threads of said sleeve means at the time of installation for ensuring a water tight seal between said sleeve means and said jacket of the fiber.

7. A cylindrical fiberoptic diffuser which has substantially uniform light output in an outwardly cylindrical scattering pattern and can be used in a biological environment, comprising:

an optical fiber with a jacket-stripped bare core tip for emitting light energy, a thin layer of scattering medium covering said bare core tip for scattering the light, and a sleeve means with one end closed and the other end fixed on the fiber jacket adjacent to said bare core tip for enclosing said fiber core tip without touching said scattering medium coated on said fiber core tip.

8. A cylindrical fiberoptic diffuser in accordance with claim 7, wherein said sleeve means includes a closed tapered head at a desired angle with respect to the central axis of said optical fiber.

9. A cylindrical fiberoptic diffuser in accordance with claim 7 or 8, wherein said sleeve means is in threaded connection with the fiber jacket adjacent to said fiber core tip.

10. A cylindrical fiberoptic diffuser in accordance with claim 9, wherein adhesive material is added on the threads of said sleeve means or on the threads of the fiber jacket at the time of installation for ensuring a water-tight seal and strengthening the connection.

11. A cylindrical fiberoptic diffuser in accordance with claim 7, wherein said scattering medium is a composition of optical adhesive material and powdered scattering material.

12. A method for manufacture of a cylindrical fiberoptic diffuser, comprising the steps of:

removing the cladding and sheathing of an optical fiber at one end for a predetermined length for providing a bare core tip, polishing said exposed bare core tip for providing a clean and smooth surface, choosing a colorless and transparent material to the light at a predetermined wavelength and making a desired shape thereby with a longitudinal size longer than the length of said bare core tip, boring said shaped material with one end closed for providing a sleeve means, inserting said bare core tip into said sleeve means without touching the inner surface of said sleeve means, and fixing the open end of said sleeve means on the fiber jacket adjacent to said bare core tip.

13. A method in accordance with claim 12, further including a step of optically homogeneously coating a thin layer of light scattering medium on said polished bare core tip with the outer diameter of the coated fiber tip smaller than the inner diameter of said sleeve means.

14. A method in accordance with claim 12 or 13, further includes a step of tapering the closed end of said sleeve means at a predetermined angle for providing a sharpened head.

15. A method in accordance with claim 12, wherein said fixing step includes the substeps of:

(i) tapping threads on the inner surface of said sleeve means and making threads on the surface of the jacket of said fiber in the portion adjacent to said bare core tip, and (ii) adding adhesive material on said threads at the time of installation for providing a water-tight seal and strengthening the connection.

16. A spherical fiberoptic diffuser for dispersing light in a spherical scattering pattern, comprising:

an optical fiber with a jacket-stripped bare core tip at one end, a cylindrical bushing means circumferentially surrounding said bare core tip without touching it, and fixed on the fiber jacket adjacent to said bare core tip portion, and a scattering medium enclosing a portion of said bushing means and said bare core tip in a spherical form.

17. A spherical fiberoptic diffuser in accordance with claim 16, wherein said bushing means is in threaded connection with the fiber jacket.

18. A spherical fiberoptic diffuser in accordance with claim 16, wherein said scattering medium is a mixture of an optical adhesive material and the powdered scattering material.

19. A spherical fiberoptic diffuser in accordance with claim 18, wherein said scattering medium preferably consists of 5% to 20% scattering material by weight.

20. A method for manufacturing a spherical fiberoptic diffuser radiating light in a spherical scattering pattern, comprising the steps of:

removing the clading and sheathing of an optical fiber at one end for a predetermined length for providing a bare core tip, polishing said core tip for providing a clean and smooth surface, preparing a silicon rubber mold including a round container portion and a cylindrical neck container portion, slowly filling said mold with a scattering mixture, inserting said fiber tip portion into said mold filled with said scattering mixture, and curing said scattering mixture at a predetermined temperature.

21. A method in accordance with claim 20, further including a step of fixing a cylindrical bushing means onto the jacket of said fiber before said inserting step which circumferentially surrounds said bare core tip.

22. A method in accordance with claim 20, further including a pre-pour step of preparing the scattering mixture by the substeps of:
(i) mixing the adhesive material with the powdered scattering material for a predetermined time,
(ii) letting the mixture stand for a predetermined time, and
(iii) degasing said mixture with a vacuum pump for a predetermined time.

23. A method in accordance with claim 20 or 21, further including a step of adjusting the position of said fiber tip end in said filled mold or a step of adjusting the position of said fiber tip in said bushing means.

24. A composition which is used as a light scattering medium in a fiberoptic diffuser and coated on a bare core tip of an optical fiber, consists of an optical adhesive material with a refractive index matching the fiber core and a powdered scattering material with a different refractive index from said adhesive material, said scattering material ranging between 5% and 20% by weight in said composition.

25. A composition in accordance with claim 24, wherein said powdered scattering material is selected from the group consisting of sapphire powder (aluminum oxide) or diamond dust or zirconium oxide dust.

26. A composition in accordance with claim 24 or 25, wherein said powdered scattering material is preferably in the range of 5% to 15% by weight in said composition.

27. A composition in accordance with claim 26, wherein said adhesive material is an epoxy.

* * * * *